United States Patent [19]
Sato

[11] Patent Number: 4,880,012
[45] Date of Patent: Nov. 14, 1989

[54] ULTRASONIC PROBE
[75] Inventor: Shohei Sato, Osaka, Japan
[73] Assignee: Omron Tateisi Electronics Co., Kyoto, Japan
[21] Appl. No.: 144,004
[22] Filed: Jan. 15, 1988
[30] Foreign Application Priority Data
  Jan. 19, 1987 [JP] Japan .................... 62-8208
[51] Int. Cl.[4] .............................. A61B 8/00
[52] U.S. Cl. .................. 128/663.01; 73/642
[58] Field of Search ............ 128/663.01; 73/642, 73/644; 367/150; 310/335

[56] References Cited
U.S. PATENT DOCUMENTS
4,387,720 6/1983 Miller ........................ 128/663.01
4,699,150 10/1987 Kawabuchi et al. ...... 128/663.01 X Primary Examiner—Francis Jaworski
Attorney, Agent, or Firm—Wegner & Bretschneider

[57] ABSTRACT

An ultrasonic probe having a vibrator which generates and receives ultrasonic waves is disclosed. The probe includes a first acoustic lens layer provided on the emergent/incident surface of the probe and a second acoustic lens layer provided on the first acoustic lens layer, the second acoustic lens layer having an attenuation constant which is different from that of the first acoustic lens layer. Accordingly, it is possible to make uniform the ultrasonic attenuation factor at various points of the acoustic lens while minimizing the attenuation factor at each of the points. Thus, it is possible to focus acoustic beams and hence obtain a clear ultrasonic image.

1 Claim, 2 Drawing Sheets

ULTRASONIC PROBE

BACKGROUND OF THE INVENTION

1. Field of the Invention

The present invention relates to an ultrasonic probe for use in an ultrasonic diagnostic apparatus or the like.

2. Description of the Related Art

One type of conventional ultrasonic probe for use in an ultrasonic diagnostic apparatus or the like is known as a linear electronic scanning type ultrasonic probe in which rectangular piezo-electric members are disposed linearly.

This type of ultrasonic probe has, as shown in FIG. 4, a vibrating portion 2 defined by a plurality of piezo-electric vibrators 1 which are disposed linearly, an acoustic absorber 3 provided at the reverse side of the vibrating portion 2, an acoustic matching layer 4 provided at the obverse side of the vibrating portion 2, and an acoustic lens 5 provided on the upper surface of the acoustic matching layer 4, the acoustic lens 5 converging ultrasonic waves generated by the vibrating portion 2 and also the reflected ultrasonic waves from a living body in the direction of the arrow A (i.e., the slicing direction).

As a material for the acoustic lens 5, silicone rubber in which the sound velocity is about 500 m/s lower than that in water has heretofore been employed.

Since the acoustic impedance of silicone rubber is about 0.5 ($\times 10^6$ kg/ms) smaller than that of a living body, it is general practice to mix a finely-divided inorganic powder with silicone rubber to thereby improve the acoustic impedance.

This conventional practice, however, leads to the followings problems:

(A) Attenuation of the ultrasonic wave passing through the acoustic lens 5 is disadvantageously large. This unfavorable effect of the acoustic lens 5 is particularly remarkable in the case of high-frequency ultrasonic waves.

(B) Since the acoustic lens 5 has a convex configuration with a curvature, the closest to the central portion the larger the attenuation factor of the transmitted ultrasonic wave, which results in a lowering in the acoustic beam converging efficiency.

SUMMARY OF THE INVENTION

In view of the above-described circumstances, it is a primary object of the present invention to provide an ultrasonic probe which is so designed that it is possible to make uniform the ultrasonic attenuation factor at various points of the acoustic lens while minimizing the attenuation factor at each of the points, thereby enabling acoustic beams to be focused, and thus obtaining a clear ultrasonic image.

To this end, the present invention provides an ultrasonic probe having a vibrator which generates and receives ultrasonic waves, the probe comprising: a first acoustic lens layer provided on the emergent/incident surface of the probe; and a second acoustic lens layer provided on the first acoustic lens layer, the second acoustic lens layer having an attenuation constant which is different from that of the first acoustic lens layer.

By virtue of the above-described arrangement, it is possible to make uniform the ultrasonic attenuation factor at various points of the acoustic lens while minimizing the attenuation factor at each of the points. Thus, it is possible to focus acoustic beams and hence obtain a clear ultrasonic image.

BRIEF DESCRIPTION OF THE DRAWINGS

The above and other objects, features and advantages of the present invention will become clear from the following description of the preferred embodiments thereof, taken in conjunction with the accompanying drawings, in which like reference numerals denote like elements, and in which.

DESCRIPTION OF THE PREFERRED EMBODIMENTS

The present invention will be described hereinunder in detail with reference to the accompanying drawings.

Figure 1:
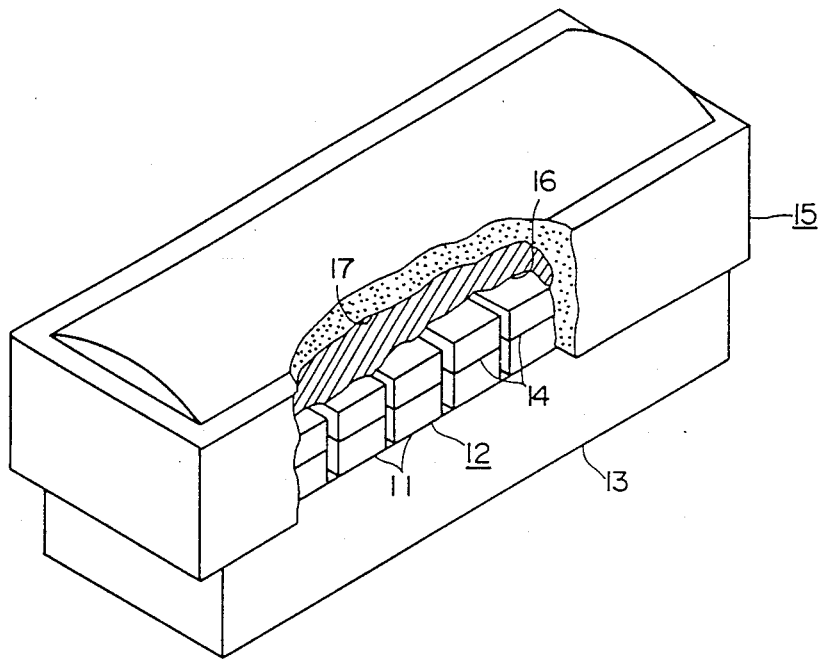
FIG. 1 is a partially-cutaway perspective view of one embodiment of the ultrasonic probe according to the present invention.

Referring first to FIG. 1, which is a partially-cutaway perspective view of one embodiment of the ultrasonic probe according to the present invention, the illustrated ultrasonic probe has a vibrating portion 12, an acoustic absorber 13, an acoustic matching layer 14 and an acoustic lens 15.

The vibrating portion 12 has a plurality of piezo-electric vibrators 11 which are disposed linearly. When the piezo-electric vibrators 11 are successively supplied with a high-frequency signal from the transmitting portion (not shown) of an ultrasonic diagnostic apparatus, the vibrators 11 successively generate ultrasonic waves. When ultrasonic waves enter the piezo-electric vibrators 11, the vibrators 11 generate electric signals corresponding to the incident ultrasonic waves and supply the signals to the receiving portion (not shown) of the ultrasonic dignostic apparatus.

The acoustic absorber 13 is a back load member which is disposed on the lower surface (as viewed in FIG. 1) of the vibrating portion 12.

The acoustic matching layer 14 is bonded (or coated) on the upper surface of the vibrating portion 12 to match the acoutic impedance of the vibrating portion 12 with the impedance of a living body.

Figure 2:
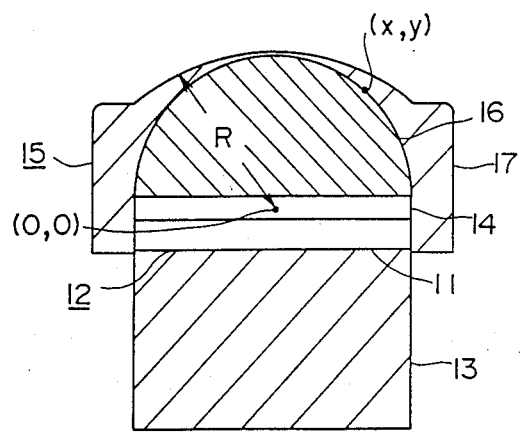
FIG. 2 is a sectional view of the ultrasonic probe shown in FIG. 1.

The acoustic lens 15 has, as shown in FIG. 2, a first lens layer 16 which is bonded to the upper surface of the acoustic matching layer 14 and a second acoustic lens layer 17 which is bonded to the upper surface of the first acoustic lens layer 16. The acoustic lens 15 converges ultrasonic waves output from the vibrating portion 12 on the focal point and also converges the reflected ultrasonic waves on the vibrating portion 12.

In this case, the first acoustic lens layer 16 is made of a silicone rubber containing no filler, for example, a silicone rubber which has an acoustic impedance of about $1/5 \times 10^6$ MKS and in which the sound velocity is about 1000 m/s.

The second acoustic lens layer 17 is made of a silicone rubber containing a filler, for example, aluminum oxide, to increase its ultrasonic attenuation coefficient.

The configurations of the first and second lens layers 16, 17 are set so that the relationship between the curvature radius R of the second acoustic lens layer 17 and the coordinates (x, y) of each point on the junction between the acoustic lens layers 16, 17 meets the condition expressed by the following equation:

$$\alpha \cdot R = \alpha \cdot y + \beta(\sqrt{R^2 - x^2 - y}) \quad (1)$$

where $\alpha$: the attenuation constant of the first acoustic lens layer 16

$\beta$: the attenuation constant of the second acoustic lens layer 17

In other words, the configurations of the first and second lens layers 16, 17 are so set that the amount of attenuation of the ultrasonic wave passing through the coordinates (0, 0) is equal to that of the ultrasonic wave passing through the coordinates (x, y). Thus, the amount of ultrasonic wave passing through every point of the acoustic lens 15 is made uniform.

As described above, in this embodiment two different kinds of silicone rubber which have different ultrasonic attenuation coefficients are employed and the thickness of the one of the silicone rubbers which has a smaller ultrasonic attenuation coefficient is increased toward the center of the acoustic lens 15. Accordingly, it is possible to make uniform the amount of ultrasonic wave passing through every point of the acoustic lens 15. Thus, it is possible to focus acoustic beams and hence obtain a clear ultrasonic image.

Figure 3:
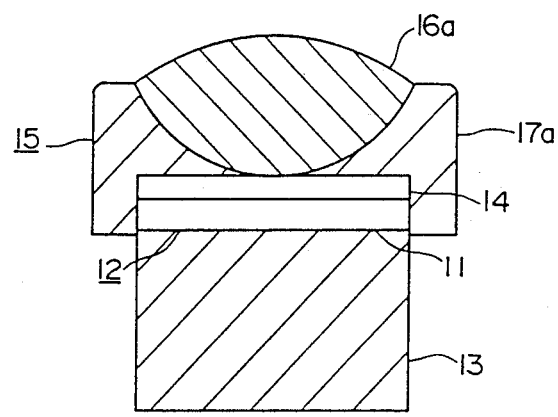
FIG. 3 is a sectional view of another embodiment of the ultrasonic probe according to the present invention.
Figure 4:
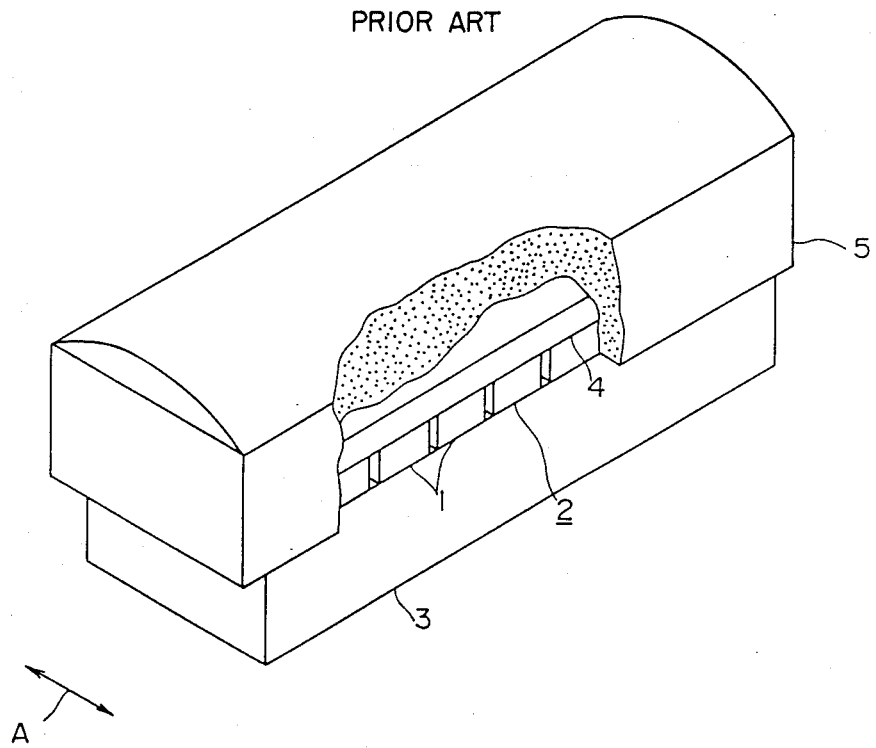
FIG. 4 is a partially-cutaway perspective view of a conventional ultrasonic probe.

FIG. 3 is a sectional view of another embodiment of the ultrasonic probe according to the present invention.

The illustrated acoustic probe differs from the probe shown in FIG. 1 in that a second acoustic lens layer 17a is disposed on the acoustic matching layer 14 and a first acoustic lens layer 16a is disposed on the second acoustic lens layer 17a.

In this embodiment also, the thicknesses of the acoustic lens layers 16a and 17a are set so that the condition expressed by the above-described equation (1) is satisfied. Therefore, it is possible to obtain advantageous effects similar to those offered by the first embodiment.

Although in the foregoing embodiments the present invention has been described by way of one example in which the invention is applied to a linear electron scanning type ultrasonic probe, the present invention may also be applied to ultrasonic probes of the phased array type, disk type or annular array type.

As has been described above, it is possible according to the present invention to make uniform the ultrasonic attenuation factor at various points of the acoustic lens while minimizing the attenuation factor at each of the points. Thus, it is possible to focus acoustic beams and hence obtain a clear ultrasonic image.

What is claimed is:

1. An ultrasonic probe comprising:
   at least one vibrator that generates and receives ultrasonic waves; and
   a composite lens disposed on the emission face of said at least one vibrator, said composite lens having a first acoustic lens layer adjacent said at least one vibrator and a second acoustic lens layer adjacent said first lens layer, said first acoustic layer having an attenuation constant at a given frequency different from the attenuation constant of said second acoustic layer at said given frequency, said second acoustic lens layer having an outer emission surface with respect to said at least one vibrator, said first acoustic lens layer and said second acoustic lens layer being configured so that the amount of attenuation of the ultrasonic wave passing through said composite lens at a point on said outer emission surface is substantially equal to that passing through said composite lens at any other point on said outer emission surface, while the focussing ability of said lens is preserved.

* * * * *